(12) United States Patent
Achkire

(10) Patent No.: US 11,684,320 B1
(45) Date of Patent: Jun. 27, 2023

(54) LINEAR MOTOR ASSEMBLY FOR X-RAY COMPUTED TOMOGRAPHY SYSTEM

(71) Applicant: Izotropic Corporation, Surrey (CA)

(72) Inventor: Younes Achkire, Surrey (CA)

(73) Assignee: Izotropic Corporation, Surrey (CA)

( * ) Notice: Subject to any disclaimer, the term of this patent is extended or adjusted under 35 U.S.C. 154(b) by 0 days.

(21) Appl. No.: 17/942,895

(22) Filed: Sep. 12, 2022

(51) Int. Cl.
  *A61B 6/03*       (2006.01)
  *A61B 6/00*       (2006.01)

(52) U.S. Cl.
  CPC ............ *A61B 6/032* (2013.01); *A61B 6/4085* (2013.01); *A61B 6/4014* (2013.01)

(58) Field of Classification Search
  CPC ...... A61B 6/032; A61B 6/4085; A61B 6/4014
  See application file for complete search history.

(56) References Cited

U.S. PATENT DOCUMENTS

| | | | |
|---|---|---|---|
| 5,526,394 | A | 6/1996 | Siczek et al. |
| 6,574,301 | B1 | 6/2003 | Jansen |
| 6,840,673 | B2 | 1/2005 | Moritake et al. |
| 7,108,421 | B2 | 9/2006 | Gregerson et al. |
| 7,242,749 | B2 | 7/2007 | Hsieh et al. |
| 7,338,207 | B2 | 3/2008 | Gregerson et al. |
| 7,404,674 | B2 | 7/2008 | Eichenseer |
| 7,437,785 | B2 | 10/2008 | Farooqui |
| 7,661,881 | B2 | 2/2010 | Gregerson et al. |
| 7,706,500 | B2 | 4/2010 | Kondo |
| 8,027,711 | B2 | 9/2011 | Jones et al. |
| 8,173,966 | B2 | 5/2012 | Caruba |
| 8,344,679 | B2 | 1/2013 | Hayes |
| 8,678,647 | B2 | 3/2014 | Gregerson et al. |
| 9,386,941 | B2 | 7/2016 | Piferi et al. |
| 9,414,790 | B2 | 8/2016 | Williams |
| 9,420,978 | B2 | 8/2016 | Gross |
| 9,498,167 | B2 | 11/2016 | Mostafavi et al. |
| 9,696,452 | B2 | 7/2017 | Schafer et al. |

(Continued)

FOREIGN PATENT DOCUMENTS

| | | |
|---|---|---|
| WO | 2018/020946 A1 | 2/2018 |
| WO | 2021/238124 A1 | 12/2021 |

OTHER PUBLICATIONS

Boone et al., "An X-ray Computed Tomography/Positron Emission Tomography System Designed Specifically for Breast Imaging", Technol Cancer Res Treat., (Feb. 2010), vol. 9, No. 1, pp. 29-44 (https://www.ncbi.nlm.nih.gov/pmc/articles/PMC3051345/pdf/nihms275387.pdf).

*Primary Examiner* — Courtney D Thomas

(74) *Attorney, Agent, or Firm* — Venable LLP; Henry J. Daley; Aziz H. Poonawalla

(57) ABSTRACT

An x-ray system for at least one of breast examinations and procedures includes a base component, a table configured to support a patient in a prone position and disposed proximate to the base component with a space reserved therebetween, a rotatable x-ray assembly disposed between the base component and the table, and a linear motor assembly operatively connected to the rotatable x-ray assembly and the base component so as to effect rotation of the rotatable x-ray assembly relative to the base component during operation. The rotatable x-ray assembly rotates at least partially around an active spatial region, and the table defines an opening that is positioned for a breast to extend downwards therethrough at least partially into said active spatial region.

18 Claims, 9 Drawing Sheets

(56) References Cited

U.S. PATENT DOCUMENTS

| | | |
|---|---|---|
| 9,826,949 B2 | 11/2017 | Ning et al. |
| 9,968,502 B2 | 5/2018 | Hight et al. |
| 9,974,494 B2 | 5/2018 | Mostafavi et al. |
| 9,986,960 B2 | 6/2018 | Ay et al. |
| 10,004,650 B2 | 6/2018 | Guertin et al. |
| 10,117,627 B2 | 11/2018 | Wagner et al. |
| 10,485,491 B2 | 11/2019 | Ning et al. |
| 10,537,296 B2 | 1/2020 | Hasegawa |
| 10,653,377 B2 | 5/2020 | Ito |
| 10,881,878 B2 | 1/2021 | Guertin et al. |
| 2005/0033141 A1 | 2/2005 | Collins et al. |
| 2006/0009696 A1 | 1/2006 | Hanover et al. |
| 2008/0089471 A1* | 4/2008 | Kobayashi ........... A61B 6/0414 378/37 |
| 2008/0212743 A1 | 9/2008 | Gregerson et al. |
| 2011/0122990 A1 | 5/2011 | Dafni |
| 2013/0243151 A1 | 9/2013 | Shih |
| 2014/0205074 A1 | 7/2014 | Gregerson et al. |
| 2016/0242703 A1 | 8/2016 | Sadakane et al. |
| 2017/0112454 A1* | 4/2017 | Yun .................... A61B 6/54 |
| 2018/0132814 A1 | 5/2018 | Noda et al. |
| 2019/0046138 A1 | 2/2019 | Dippl et al. |
| 2019/0142353 A1 | 5/2019 | Stegehuis et al. |
| 2021/0153825 A1 | 5/2021 | Shizukuishi |
| 2021/0169431 A1 | 6/2021 | Boone et al. |
| 2021/0228175 A1 | 7/2021 | Siegel et al. |

* cited by examiner

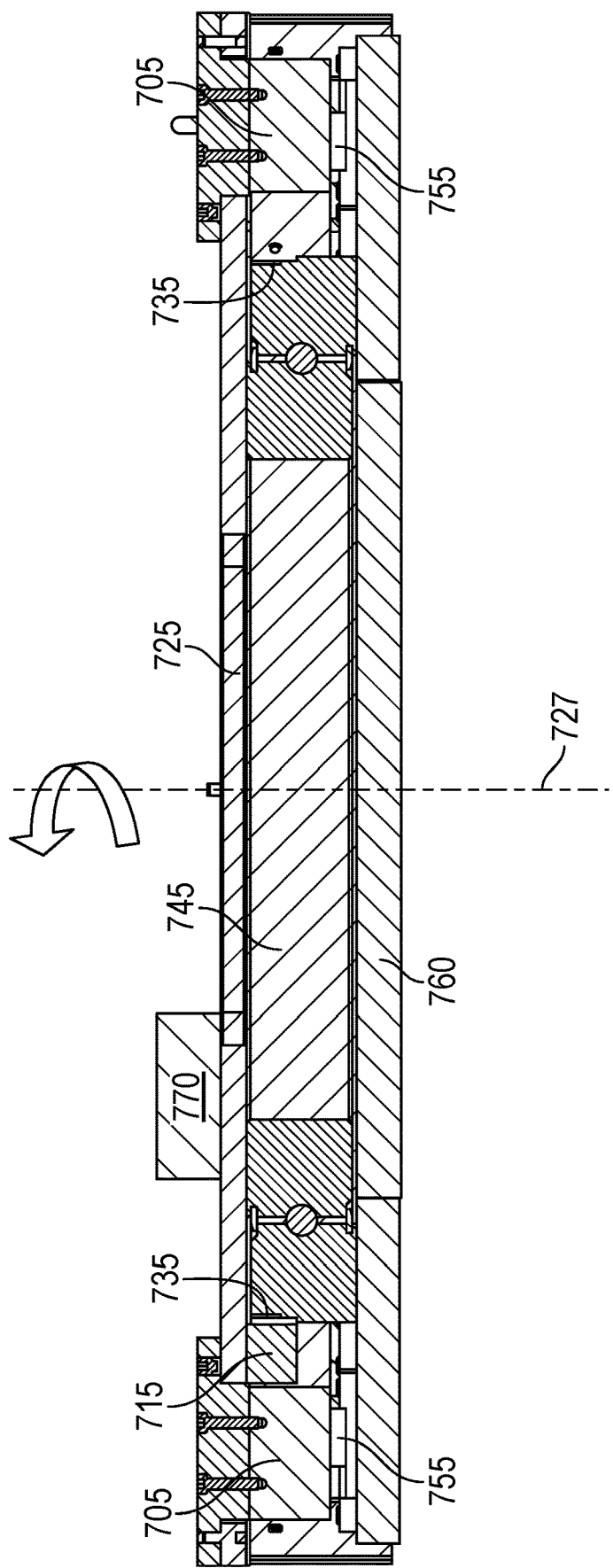

LINEAR MOTOR ASSEMBLY FOR X-RAY COMPUTED TOMOGRAPHY SYSTEM

BACKGROUND

1. Technical Field

Currently claimed embodiments of the invention relate to systems and components for breast examination and procedures, and more particularly to systems that have a linear motor.

2. Discussion of Related Art

While the current state-of-the-art for breast imaging is typically digital mammography, sometimes coupled with limited angle tomography which is often called breast tomosynthesis, it is recognized by the breast imaging community that these two-dimensional or pseudo-three-dimensional imaging modalities do not fully address the needs of breast cancer detection, diagnosis, and evaluation. Several groups have studied the use of computed tomography principles for breast imaging. These studies generally describe imaging a single breast at a time with the patient laying prone on a table, with the patient's breast hanging through a hole in the table in so-called pendant position. The x-ray CT system then rotates around the pendant breast and acquires data which is then reconstructed into a three-dimensional image.

However, such conventional breast CT systems are bulky due at least partially to the motor assemblies, and lack precision in angular rotations. There thus remains a need for improved breast CT systems.

SUMMARY

An embodiment of the present invention is an x-ray system for at least one of breast examinations and procedures. The x-ray system includes a base component, a table configured to support a patient in a prone position and disposed proximate to the base component with a space reserved therebetween, a rotatable x-ray assembly disposed between the base component and the table, and a linear motor assembly operatively connected to the rotatable x-ray assembly and the base component so as to effect rotation of the rotatable x-ray assembly relative to the base component during operation. The rotatable x-ray assembly rotates at least partially around an active spatial region, and the table defines an opening that is positioned for a breast to extend downwards therethrough at least partially into the active spatial region.

Another embodiment of the present invention is an assembly for use with an x-ray system for at least one of breast examinations and procedures. The assembly includes a base component, a rotatable x-ray assembly arranged proximate to and spaced apart from the base component, and a linear motor assembly operatively connected to the base component and the rotatable x-ray assembly so as to effect rotation of said rotatable x-ray assembly relative to the base component during operation. The rotatable x-ray assembly includes a shield enclosure defining an internal region therein, an x-ray source attached to the shield enclosure, the x-ray source being arranged to irradiate with an x-ray beam at least a portion of an active spatial region, and an x-ray detector attached to the shield enclosure, the x-ray detector being arranged to receive at least a portion of the x-ray beam after passing through the active spatial region. The shield enclosure attenuates x-rays from the x-ray source sufficiently for people to be in proximity to the shield enclosure during operation of the x-ray system without further shielding while complying with radiation safety standards.

Another embodiment of the present invention is a method of manufacturing an x-ray system for at least one of breast examinations and procedures. The method includes providing a base component, and disposing a table proximate to the base component with a space reserved therebetween, the table configured to support a patient in a prone position. The method further includes disposing a rotatable x-ray assembly between the base component and the table, and connecting a linear motor assembly to the rotatable x-ray assembly and the base component so as to be operative to effect rotation of the rotatable x-ray assembly relative to the base component. The rotatable x-ray assembly rotates at least partially around an active spatial region, and the table defines an opening therethrough at a position and of a size to allow a subject to lie prone with a breast hanging pendant therethrough at least partially into the active spatial region.

Another embodiment of the present invention is a method of performing a breast procedure. The method includes receiving x-ray data acquired from a rotatable x-ray assembly, the rotatable x-ray assembly disposed between a base component and a table configured to support a patient in a prone position. The method further includes receiving information from an encoder assembly, the encoder assembly being arranged proximate to a linear motor assembly that is operatively connected to the rotatable x-ray assembly and the base component so as to effect rotation of said rotatable x-ray assembly relative to the base component during operation of the x-ray assembly. The method further includes determining at least one of an amount of rotation and a rotation position of the rotatable x-ray assembly during acquisition of the x-ray data, and generating multiple x-ray images based on the received x-ray data and at least one of the determined amount of rotation and the rotation position of the rotatable x-ray assembly.

BRIEF DESCRIPTION OF THE DRAWINGS

Further objectives and advantages will become apparent from a consideration of the description, drawings, and examples.

FIG. 7 shows an example of a configuration for a linear motor assembly of some embodiments.

DETAILED DESCRIPTION

Figure 1:
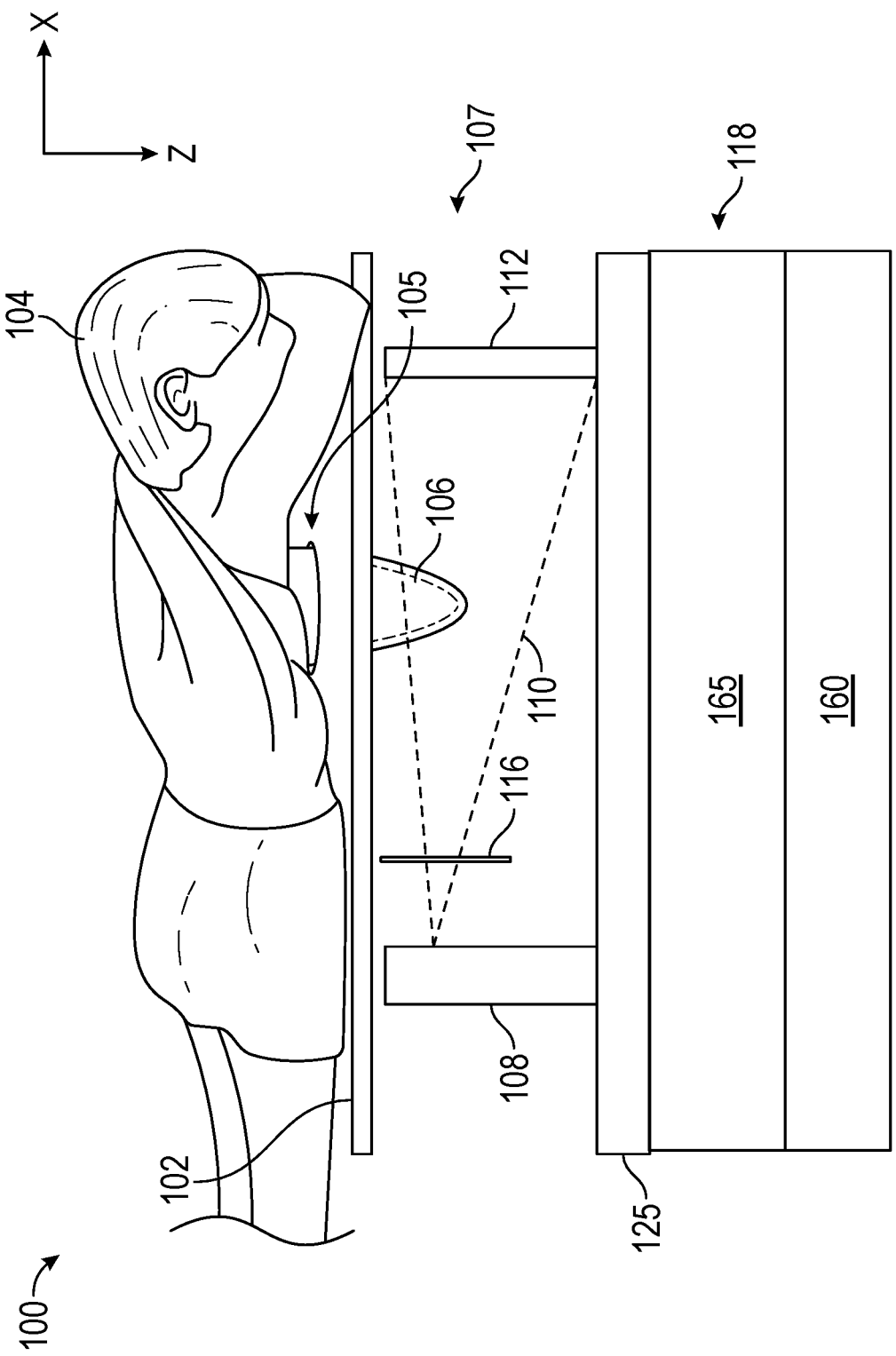
FIG. 1 shows a schematic of an x-ray system of some embodiments, for breast examinations and procedures.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed, and other methods developed, without departing from the broad concepts of the current invention.

All references cited anywhere in this specification, including the Background and Detailed Description sections, are incorporated by reference as if each had been individually incorporated.

The term "linear motor" as used herein is intended to refer to a type of electric motor that has its stator and rotor "unrolled," in a sense. For example, instead of producing a torque (rotation), a linear motor produces a linear force along its length. The length of the linear motor can be arranged as a straight or as a curved line. In some embodiments, the length of the linear motor can be in a closed loop such as, but not limited to, a circular loop. Synchronous linear motors are a type of linear motors with a stationary magnetic rail that acts as the stator, and a moving electromagnetic coil that acts as the rotor.

The term "active spatial region" is intended to refer to a region of space where at least a portion of an object or a subject can be positioned during x-ray breast examinations and procedures. For example, the active spatial region may be defined by the field of view (FOV) of the imaging detector, referred to as the "imaging FOV."

The term "base component" is intended to be a structural support for a rotating assembly. For example, the base component may support a bearing for a rotating gantry. In some embodiments, the base component can be placed upon a floor, or is a floor, of a room in which the rotating assembly is located. The term "base support" may be used equivalently to the term "base component."

In some embodiments, the "x-ray assembly" can include an x-ray source and/or an x-ray detector. In some embodiments, the x-ray assembly can also include a rotating gantry to which the x-ray source and the x-ray detector are mounted. For example, in some embodiments, the x-ray detector can be a flat-panel detector. In some embodiments, the x-ray assembly includes a shield that substantially encloses the x-ray source and the x-ray detector. The term "rotatable x-ray assembly" may include, but is not limited to, systems for computed tomography (CT), cone-beam CT (CBCT), fan-beam CT, radiation therapy (e.g., x-ray therapy), and x-ray surgery (e.g., biopsy).

The term "shield enclosure" is intended to refer to an enclosure that substantially encloses the x-ray source and x-ray detector of an x-ray assembly, and provides radiation protection to persons in proximity to the x-ray assembly. In some embodiments, the radiation shield enclosures described in U.S. patent application Ser. No. 17/727,540 can be used. U.S. patent application Ser. No. 17/727,540, which was filed on Apr. 22, 2022, is incorporated herein by reference in its entirety.

The term "runout" is intended to refer to the maximum amount a rotating surface may vary during rotation of that surface about an axis. The runout refers to both the amount of variation in the surface as the part is rotated, and the amount of variation in the axial dimension. Both radial variation and axial variation are measured and held within a manufacturing-specified tolerance. These variations are said to "stack up" because they are cumulative.

FIG. 1 shows an example of an x-ray system 100 of some embodiments, for breast examinations and procedures. The x-ray system 100 includes a table 102 configured to support a patient 104 in a prone position, and has an opening 105 that is positioned so that the patient's breast 106 extends downwards through the opening 105 into an active spatial region, also referred to as the imaging field of view (FOV), for the x-ray system 100.

The x-ray system 100 includes a rotatable x-ray assembly 107 disposed in a reserved space beneath the table 102. The x-ray assembly 107 includes, for example, at least one x-ray source 108 that generates an x-ray beam 110, and an x-ray detector 112. In various embodiments, the x-ray detector 112 may be a flat panel detector, the x-ray beam 110 may be a cone beam, and the x-ray system 100 may be configured to perform cone-beam computed tomography.

The at least one x-ray source 108 is positioned to irradiate, with the x-ray beam 110, at least a portion of the imaging FOV into which the breast 106 extends. The x-ray detector 112 is positioned to receive at least a portion of the x-ray beam 110 after passing through the imaging FOV and at least a portion of the breast 106. The x-ray beam 110 may be collimated by a collimator 116 before irradiating at least a portion of the breast 106 and thereafter impinging on the x-ray detector 112.

A gantry assembly 118 is positioned beneath the table 102, and includes a gantry platform 125, a base 160, and a linear motor assembly 165 that is operatively connected to the rotatable x-ray assembly 107. During operation, the linear motor assembly 165 exerts a torque upon the gantry platform 125 in order to rotate the gantry platform 125 relative to the base 160 around the breast 106 and the surrounding active spatial region (e.g., the imaging FOV). In some embodiments, the base 160 and the table 102 are configured to be fixed relative to each other. In some embodiments, the x-ray source 108 and the x-ray detector 112 are rigidly mounted to the gantry platform 125 so as to also rotate around the breast 106 and the imaging FOV during rotation of the gantry platform 125 by the linear motor assembly 165.

In some embodiments, the x-ray system 100 may have a static subsystem (e.g., stationary components of the x-ray system 100 including but not limited to the table 102) and a rotating subsystem (e.g., rotatable components of the x-ray system 100 including but not limited to the x-ray source 108 and the x-ray detector 112) that is rotated by the linear motor assembly 165.

In some embodiments, the linear motor assembly 165 is an electromagnetic motor that includes components such as magnet rails and magnetic coils. The linear motor assembly 165 may also include a position encoder, e.g., an external high-precision encoder. The linear motor assembly 165 may also include a bearing (see FIG. 2B) that is capable of providing stiffness for the rotating subsystem, based on the forces and moment load applied to it.

The linear motor assembly 165 of some embodiments may provide a number of advantages over other motor types, such as shaft-driven motors. These advantages may include some or all of, but are not limited to, providing a compact motor in height (to lower the patient table for better accessibility and user comfort), a custom-designed stiffness response of the bearing depending on the operational mode or application of the x-ray system 100 (e.g., breast examinations, procedures, etc.), high positional precision with quantified angle measurement at large effective radius of rotation (to properly reconstruct the CT images acquired at different views of the breast), high torque (sufficient to rotate the gantry plus the weight of the imaging system supported thereby) with fewer coils because of the larger effective radius, and increased cost-effectiveness.

In some embodiments, the x-ray system 100 also includes a shield enclosure (not shown in FIG. 1) that substantially encloses the x-ray source 108, the x-ray detector 112, and the imaging FOV. Accordingly, during operation of the x-ray system 100, the shield enclosure also substantially encloses the x-ray beam 110 generated by the x-ray source 108. The shield enclosure attenuates x-rays from the x-ray source 108 sufficiently for persons to be in proximity to the shield enclosure during operation of the x-ray system 10 without further shielding, while complying with radiation safety standards. The shielding enclosure may also be rigidly mounted to the gantry platform 125, and thereby rotates around the breast 106 with the x-ray source 108 and the x-ray detector 112.

A number of embodiments of a linear motor assembly for an x-ray system are now described, and wherever possible, like reference numerals have been used to refer to the same or similar components. Any of the various features discussed with any one of the embodiments discussed herein may also apply to and be used with any other embodiments.

Figure 2A:
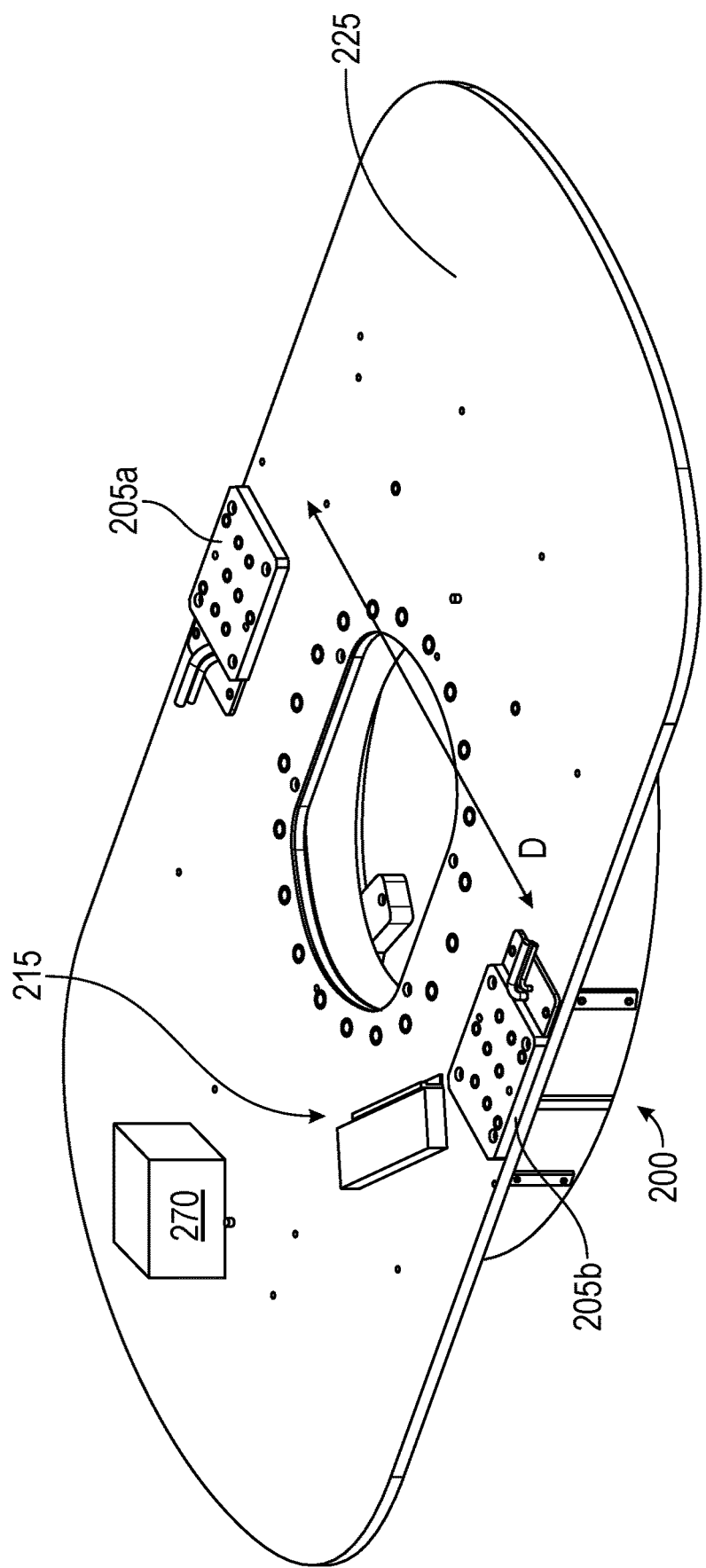
FIG. 2A shows an example of a linear motor assembly of some embodiments.
Figure 2B:
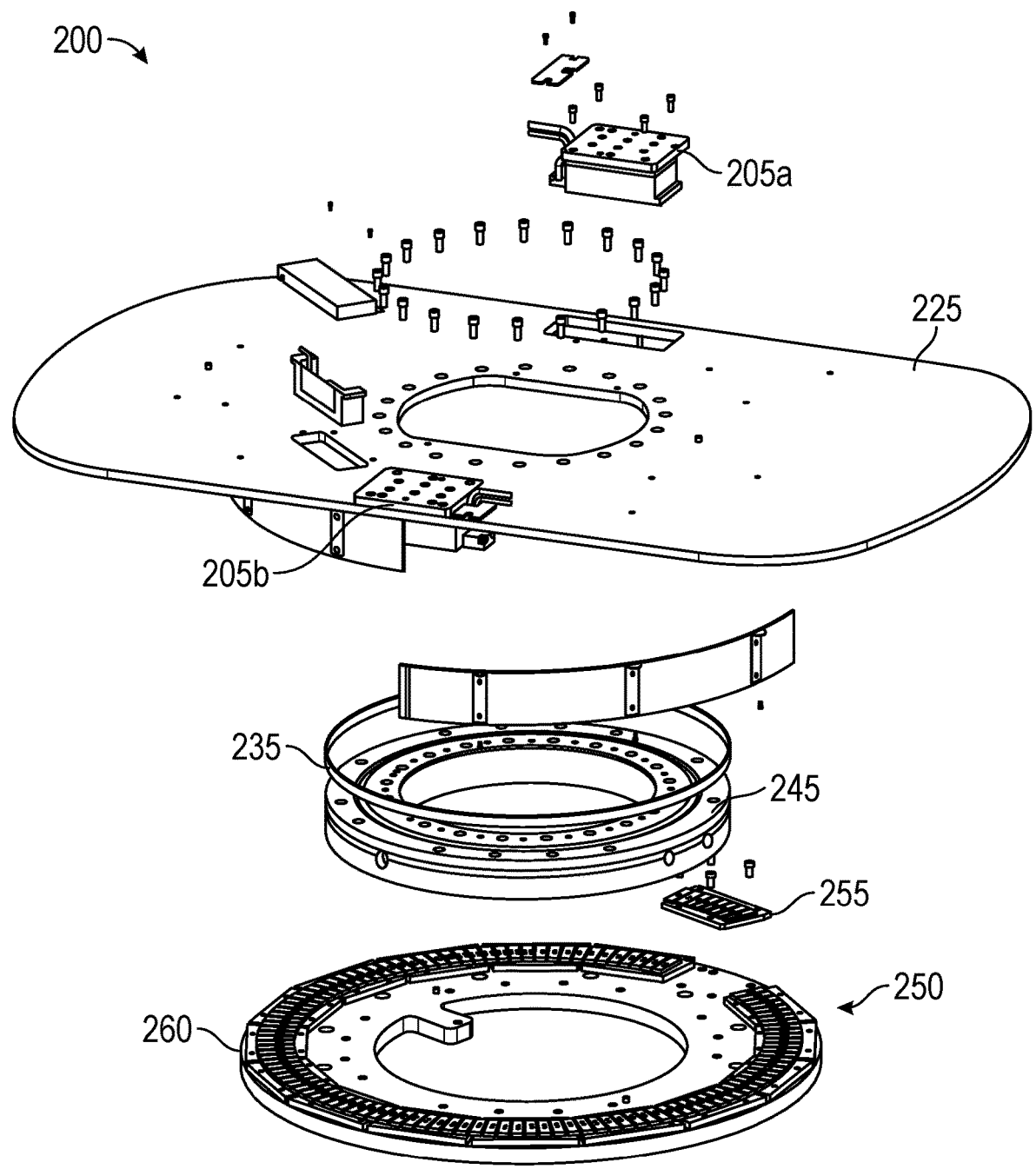
FIG. 2B shows an exploded view of the linear motor assembly of FIG. 2A.

FIG. 2A shows a linear motor assembly 200 of some embodiments. FIG. 2B provides an exploded view of the linear motor assembly 200. In this example, the linear motor assembly 200 has two coil assemblies 205a, 205b, and an encoder assembly 215. Though two coil assemblies are shown, in other embodiments, there may be a single coil assembly, or more than two. The coil assemblies 205a, 205b act as the rotor for the linear motor assembly 200.

In this example, the coil assemblies 205a, 205b, and encoder assembly 215 of the linear motor assembly 200 are rigidly mounted to a gantry platform 225 (also referred to as a gantry plate, or a gantry support). The coil assemblies 205a, 205b are positioned on opposite sides of the gantry platform 225, separated by a distance D. (See FIG. 2A.) This distance defines an effective radius of rotation (e.g., equal to D/2) for the linear motor assembly 200. Beneath the gantry platform 225, an encoder scale 235 is positioned so that it may be read by the encoder assembly 215. The gantry platform 225 is supported upon a bearing 245 and rotates thereupon. A magnet ring assembly 250 comprised of magnet rails 255 is placed around the circumference of the bearing 245, positioned proximal to the coil assemblies 205a, 205b so as to generate a torque upon the bearing 245 during operation of the coil assemblies 205a, 205b. The magnet rails 255 thereby act as stators for the linear motor assembly 200. At least a portion of the linear motor assembly 200 is supported by a stationary, electrically-grounded base support 260.

In some embodiments, the x-ray system 100 also includes a data processor 270 communicatively coupled to the encoder assembly 215 and configured to, based on information received from the encoder assembly 215, determine at least one of the amount of rotation and the rotation position of the gantry platform 225, and accordingly, the amount of rotation and the rotation position of any x-ray assembly mounted thereupon.

The linear motor assembly 200 is configured to rotate between six to twelve rotations per minute (RPM) in some embodiments. In some embodiments, the linear motor assembly 200 is configured to support an axial load (in a downwards direction along the axis of rotation) of up to 500 pounds, or 300 kilograms, due to the added weight of the components mounted on the gantry platform 225. When the axial load on the gantry platform 225 is fully balanced, then the bearing 245 has a moment load of zero. If the axial load on the gantry platform 225 is imperfectly balanced, then the total load of the bearing 245 includes a non-zero moment load in addition to the axial load. If a radial load (in an inwards direction perpendicular to the axis of rotation) is present, then that radial load may also contribute to the total load upon the bearing. The linear motor assembly 200 may be configured and balanced to substantially reduce the moment load and to substantially eliminate the radial load.

In some embodiments, the number of coil assemblies is defined by the motor torque, which is driven by a number of characteristics of the linear motor assembly 200, including but not limited to bearing friction load torque, gantry inertia torque, speed, acceleration, and linear motor cogging torque. The coil assemblies 205a, 205b may be equally spaced on the effective radius of rotation so as to not add any additional moment to the bearing 245, or may be unequally spaced to provide some counter moment if needed, due to other components such as the x-ray assembly 107.

Figure 2C:
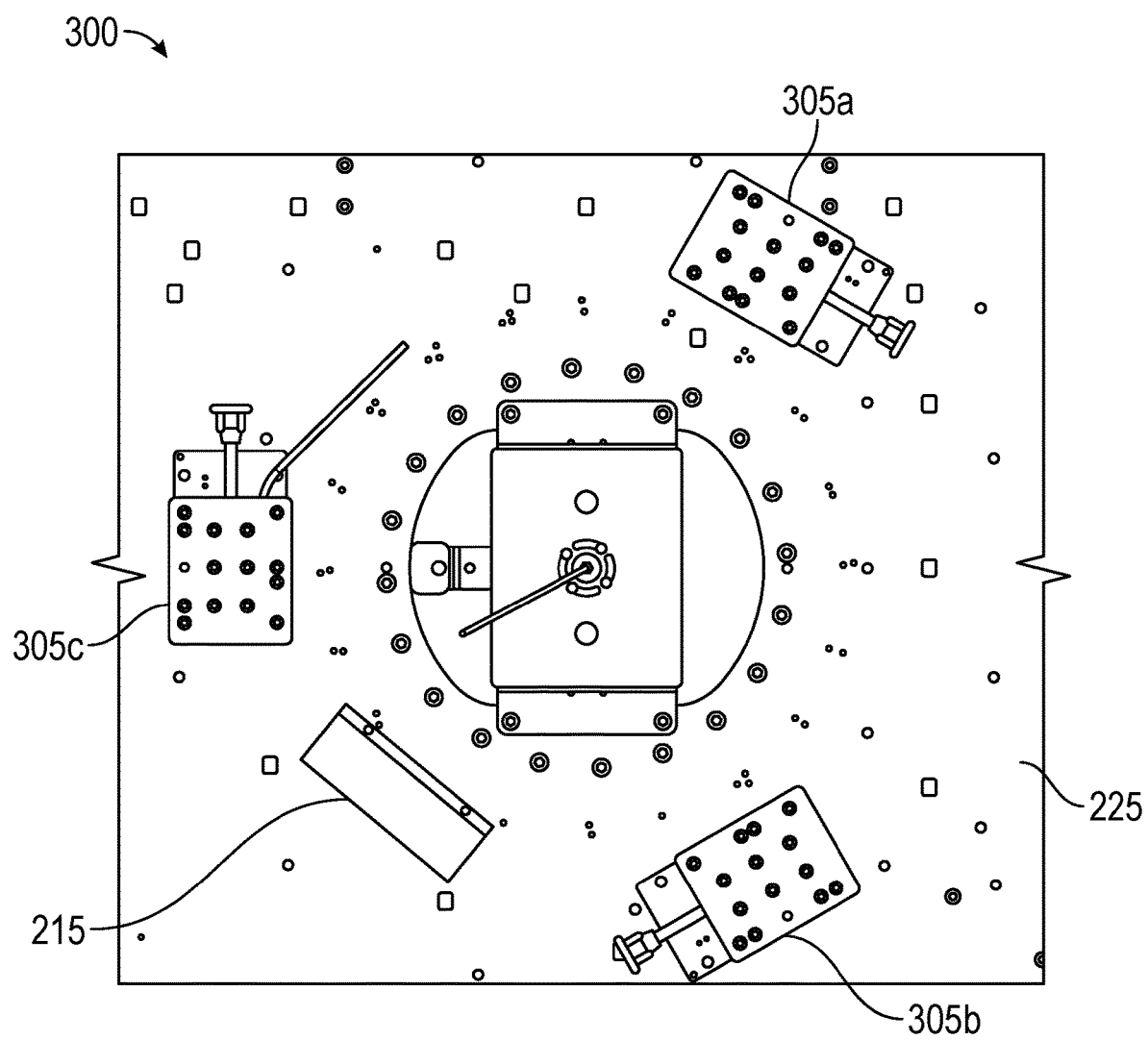
FIG. 2C shows another example of a linear motor assembly of some embodiments.

FIG. 2C shows an alternative configuration of a linear motor assembly 300 of some embodiments. In this example, the linear motor assembly 300 has three coil assemblies 305a, 305b, 305c, and an encoder assembly 315, mounted to the gantry platform 225. The use of three coil assemblies may provide greater torque than a two-coil configuration, greater precision in rotational motion, and improved counter moment to the bearing 245 (not shown in FIG. 2C).

Figure 3:
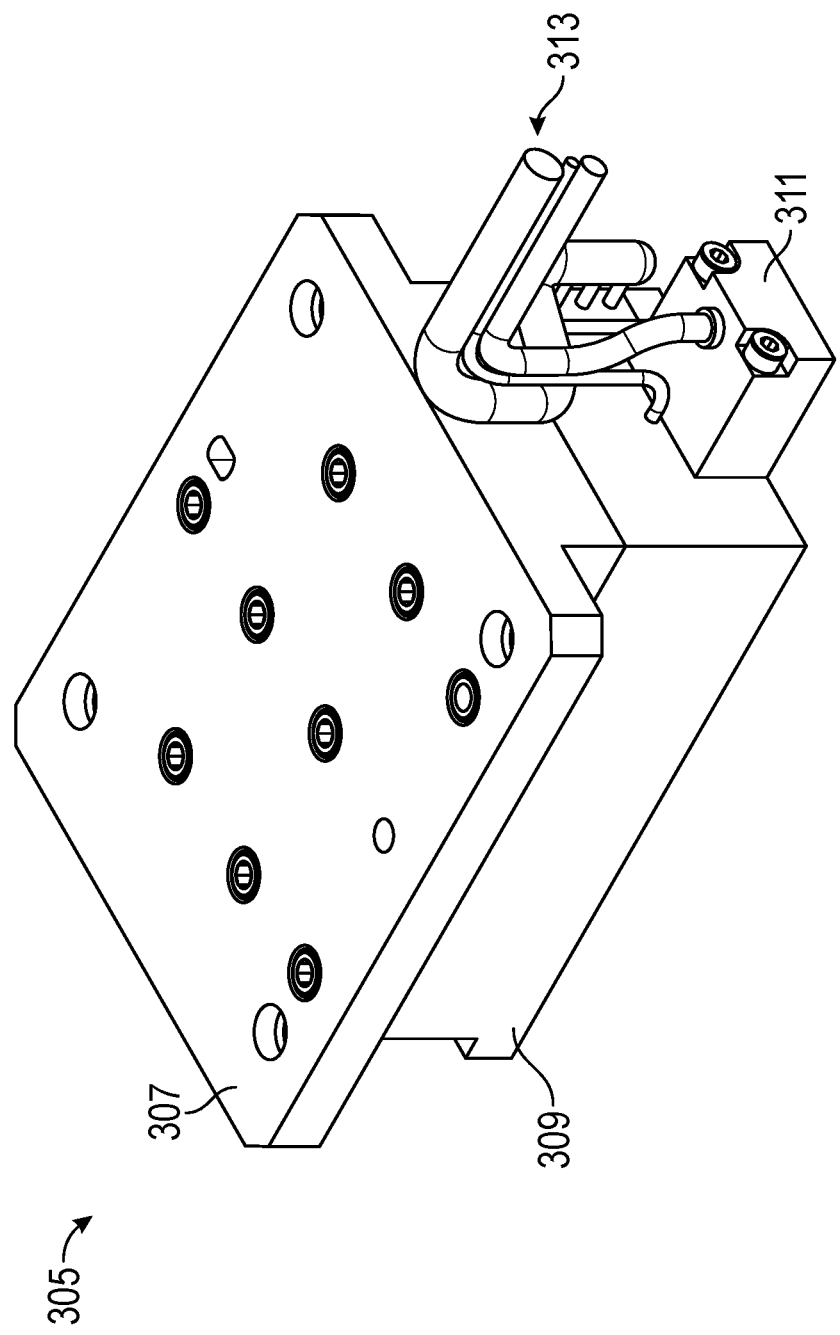
FIG. 3 shows a coil assembly of some embodiments.
Figure 8:
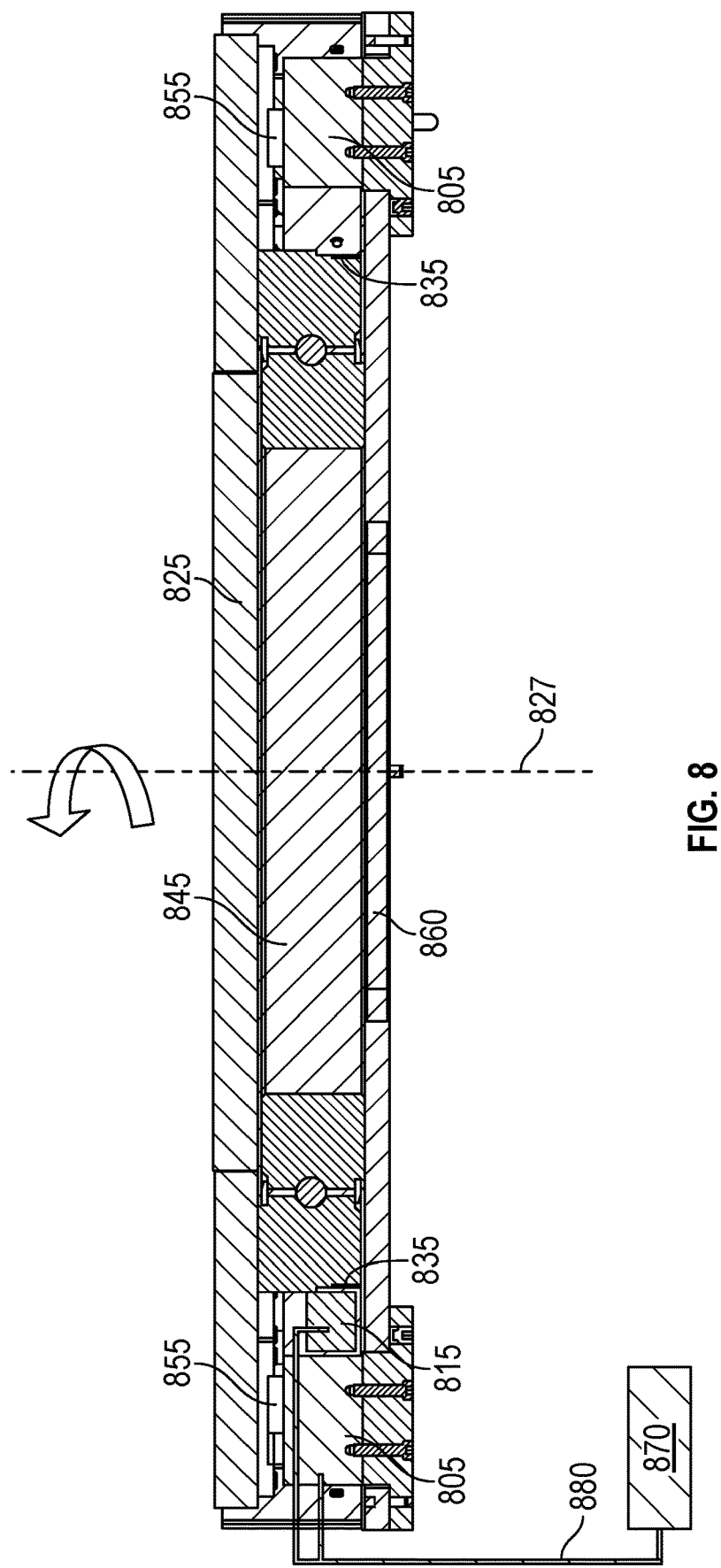
FIG. 8 shows another example of a configuration for a linear motor assembly of some embodiments.

FIG. 3 shows a coil assembly 305 of some embodiments. The coil assembly 305 may be used, as non-limiting examples, for some or all of the coil assembly 205a, the coil assembly 205b, the coil assembly 305a, the coil assembly 305b, the coil assembly 305c, the coil assembly 705 (FIG. 7), and the coil assembly 805 (FIG. 8). The coil assembly 305 includes a coil mount 307, a magnetic coil 309, and a Hall sensor 311. The coil mount 307 enables the coil assembly 305 to be rigidly mounted to either the gantry platform 225 (not shown in FIG. 3) or to the base support 260. The Hall sensor 311 provides switching of the magnetic field (referred to as commutation) of the magnetic coil 309 in order to alternately attract and repel the magnets in the magnet rails 255, and thereby create a consistent directional force tangent to the magnet rails 255, in order to propel the rotor (the magnetic coil 309) along the stator (the magnet rails 255). In the example shown in FIG. 3, the coil assembly 305 also includes umbilical cables 313 that provide power and control signals to and from the magnetic coil 309.

Figure 4:
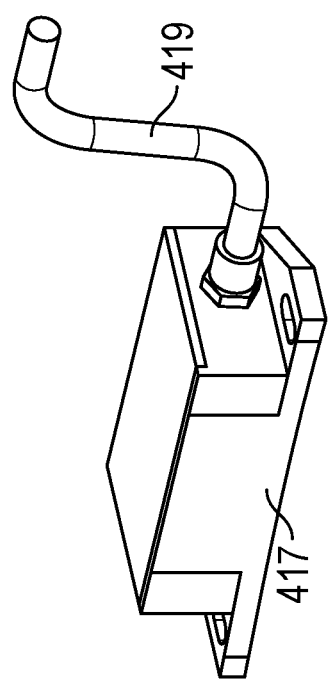
FIG. 4 shows an encoder assembly of some embodiments.

FIG. 4 shows an encoder assembly 415 of some embodiments, arranged proximate to the linear motor assembly 400. The encoder assembly 415 may be used, as non-limiting examples, as some or all of the encoder assembly 215, the encoder assembly 715 (FIG. 7), and the encoder assembly 815 (FIG. 8). The encoder assembly 415 may be constructed to provide information regarding at least one of an amount of rotation and a rotational position of the rotatable x-ray assembly 107 relative to the base 160. In this example, the encoder assembly 415 includes an encoder sensor head 417, which is positioned facing towards a positional encoder. For example, in some embodiments, the encoder sensor head 417 may be an optical sensor, and the positional encoder may be an encoder scale 235 that has a grating or markings that can be optically detected by the encoder sensor head 417. Any suitable sensor and corresponding encoder scale may be used, however, including but not limited to magnetic sensors, electrical sensors, and radiofrequency sensors. In some embodiments, the encoder assembly 415 is a Transistor-Transistor-Logic (TTL) assembly, that provides a constant output signal level when activated, regardless of the supply voltage level. In the example of FIG. 4, the encoder assembly 415 includes a cable 419, which is connected to a data processor (not shown), and through which the encoder assembly 415 provides an output signal to the data processor.

Figure 5A:
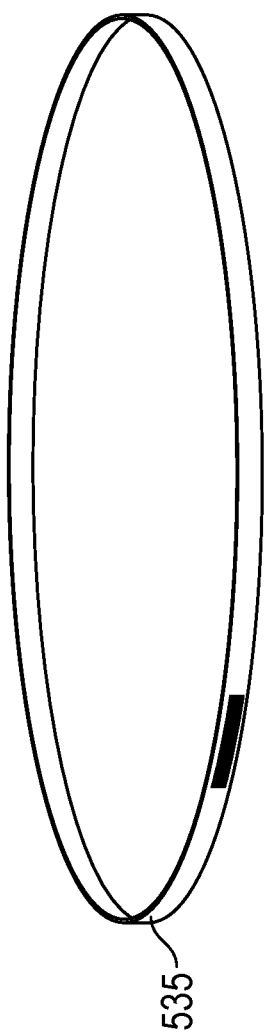
FIG. 5A shows an encoder scale of some embodiments.
Figure 5B:
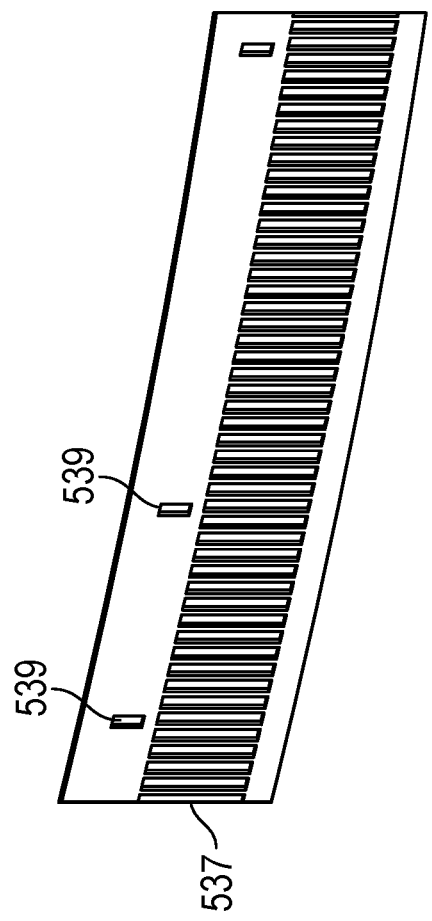
FIG. 5B shows a detail view of the encoder scale of FIG. 5A.

FIG. 5A shows an encoder scale 535 of some embodiments. The encoder scale 535 may be used, as non-limiting examples, as one or more of the encoder scale 235, the encoder scale 735 (FIG. 7), and the encoder scale 835 (FIG. 8). FIG. 5B shows a detail view of a section of the encoder scale 535 in FIG. 5A. In this example, the encoder scale 535 is a ring-shaped grated tape, which has a pitch grating 537 along the outer surface. As an example, the pitch grating 537 may be a 3 millimeter pitch grating with 540 counts evenly spaced around the circumference of the encoder scale 535, resulting in an angular resolution that is less than ±0.32 degrees in some embodiments, and is ±0.25 degrees or less in preferred embodiments. In addition, in some embodiments the encoder scale 535 also has coded marks 539 that are unevenly spaced. Upon receiving a signal from the encoder assembly 415 (FIG. 4) indicating detection of two consecutive coded marks 539, the data processor (not shown in FIG. 5B) may be configured to determine an absolute angular position of the encoder assembly 415. This absolute position may be used in a homing routine, for example, in which the linear motor resets to a predefined angular position. The data processor may use a lookup table in some embodiments to determine the absolute position, based on which consecutive coded marks 539 are detected by the encoder assembly 415 during operation. The absolute position may be determined either upon receiving an instruction from a user, in real time on a continuous or periodic basis, or both.

Figure 6B:
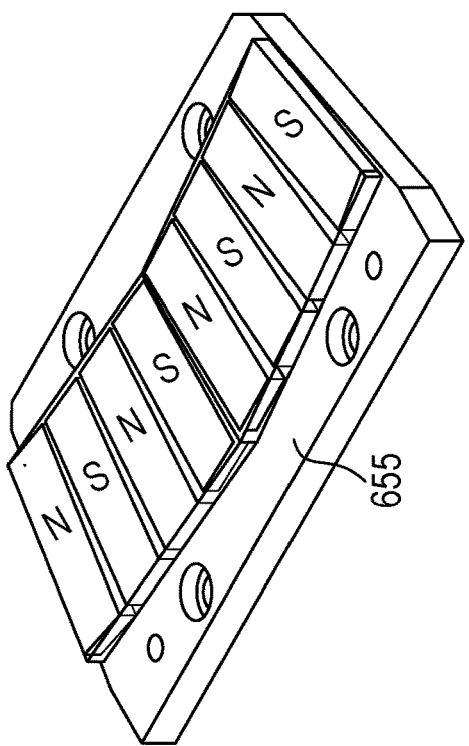
FIG. 6B shows a detail view of a magnet rail for the magnet rail assembly of FIG. 3A.
Figure 6A:
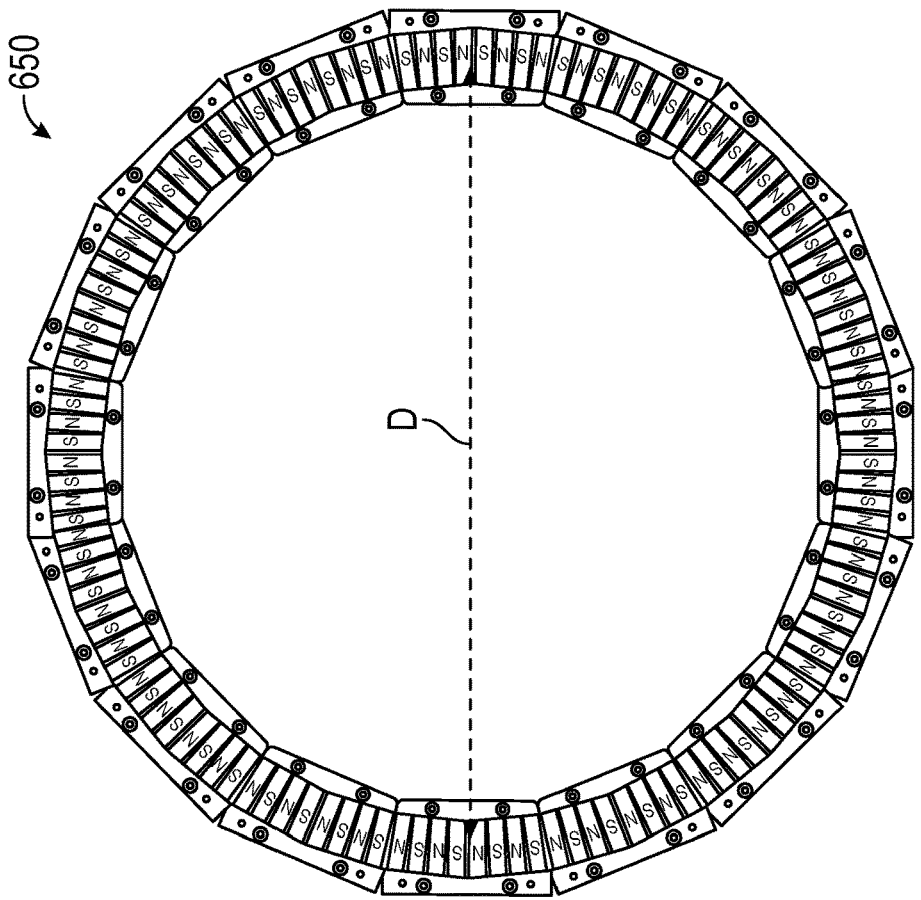
FIG. 6A shows a magnet rail assembly of some embodiments.

FIG. 6A shows a magnet rail assembly 650 of some embodiments. The magnet rail assembly 650 may be used, as non-limiting examples, as the magnet rail assembly 250. The magnet rail assembly 650 includes multiple magnet rails 655 positioned in a circular arrangement, with effective radius R. FIG. 6B shows a detail view of an individual magnet rail 655 for the magnet rail assembly 650 of FIG. 3A. The magnet rail 655 may be used, as non-limiting examples, as one or more of the magnet rail 255, the magnet rail 755 (FIG. 7), and the magnet rail 855 (FIG. 8). In this example, each magnet rail 655 is an assembly of eight permanent magnets laid side by side, with alternating polarity. Four of the permanent magnets are positioned with magnetic north polarity facing upwards, and the other four are positioned with magnetic south polarity facing upwards, placed in an interleaved fashion. In some embodiments, the magnet rails 655 are electromagnets or other types of magnets rather than permanent magnets.

In other embodiments, there may be a different number of permanent magnets in each magnet rail 655. In this example, sixteen such magnet rails 655 are used to complete the circle. In other embodiments, the magnet rails 655 may be a different size (e.g., there may be a different number of permanent magnets in the magnet rail 655, or the radius of curvature may be different) and therefore a different number of magnet rails 655 may be used to achieve a different effective diameter D, depending on the design requirements for the x-ray system. The effective diameter D is designed to match the effective radius of rotation of one or more coil assemblies during rotation of the gantry platform. For example, for embodiments such as that described above with reference to FIG. 2, which includes two coil assemblies 205 separated by a distance D at opposite ends of a gantry platform 225, the effective diameter D is equal to the distance D.

FIG. 7 shows an example of a configuration for a linear motor assembly 700 of some embodiments. The linear motor assembly 700 is similar in some respects to the embodiment of the linear motor assembly 200 discussed above with respect to FIG. 2A and FIG. 2B, and like reference numerals have been used to refer to the same or similar components. A detailed description of these components will be omitted, and the following discussion focuses on the differences between these embodiments.

The linear motor assembly 700 includes two coil assemblies 705 and an encoder assembly 715 that are rigidly mounted to a gantry platform 725 and rotate therewith around an axis of rotation (denoted by dashed line 727). An x-ray assembly (not shown) is also rigidly mounted to the gantry platform 725, and thereby is coupled to the coil assemblies 705 and the encoder assembly 715 to rotate therewith. The coil assemblies are separated by a distance D at opposite sides of the gantry platform 725. However, in some embodiments the coil assemblies may be positioned asymmetrically around the gantry platform 725.

Alternatively, in some embodiments, the linear motor assembly 700 may include three or more coil assemblies rigidly mounted to the gantry platform 725 to rotate therewith. In some such embodiments, the coil assemblies may be positioned equally around the circumference of the gantry platform at a distance D/2 from the axis of rotation. In other such embodiments, the coil assemblies may be positioned asymmetrically around the gantry platform 725.

The linear motor assembly 700 also includes an encoder scale tape 735 that is mounted to a stationary outer portion of a bearing 745 that rotatably supports the gantry platform 725. The encoder scale tape 735 is positioned so that it is within the field of view of a sensor head (not shown) of the encoder assembly 715 at all times during the rotation of the gantry platform 725.

In this example, the encoder scale tape 735 is mounted directly to the bearing 745 in order to minimize runout stack up tolerances. In different embodiments, the encoder scale tape 735 can be mounted on the rotating gantry platform 725, or mounted on the base support 760 if machining its feature on the bearing is impossible or not feasible. In that case the run-out stack up tolerance is larger and increases the tolerances on the gantry or bearing supports.

The bearing 745 is mounted above a stationary base support 760. A ring of multiple magnet rails 755, each defining an arc segment of a full circle, are positioned on the base support 760 around the circumference of the bearing 745, and further positioned to align with the coil assemblies 705 during rotation of the gantry platform 725. In this example, the distance between the two coil assemblies 705 is equal to the effective diameter of the ring of magnet rails 755. The magnet rails 755 are mounted on the base support 760 outside the bearing 745, though in different embodiments, the magnet rails 755 may be mounted on the base support 760 inside the bearing 745.

The gantry platform 725 and an inner portion of the bearing 745 are driven to rotate relative to the base support 760 by generating a circumferentially-directed electromagnetic force between the rotating coil assemblies 705 and the stationary magnet rails 755. During rotation of the gantry platform 725, the encoder assembly 715 rotates past the stationary encoder scale tape 735, and generates signals which are received by a processor 770. The processor 770 uses these signals to determine (e.g., in real-time) the rotation angle and position of the gantry platform 725 relative to the base support 760, as well as provide an automated "homing" instruction to rotate the gantry platform 725 to a predetermined angular position.

In this configuration, an electrical slip ring (not shown) is needed to provide power, as well as send and receive control instructions, to the coil assemblies 705 and the encoder assembly 715. Additional control electronics (e.g., a motor amplifier, not shown) and the processor 770 are mounted to the rotating gantry to minimize the size of the slip ring and minimizing the amount of cabling and wiring (not shown).

FIG. 8 shows another example of a configuration for a linear motor assembly 800 of some embodiments. The linear motor assembly 800 is similar in some respects to the embodiment of the linear motor assembly 200 discussed above with respect to FIG. 7, and like reference numerals have been used to refer to the same or similar components. A detailed description of these components will be omitted, and the following discussion focuses on the differences between these embodiments.

In similar fashion as linear motor assembly 700 described above with reference to FIG. 7, the linear motor assembly 800 includes two coil assemblies 805, an encoder assembly 815, a gantry platform 825, an encoder scale tape 835, a bearing 845, magnet rails 855, a stationary base support 860 that rotateably supports the gantry platform 825, and a processor 870. However, unlike the linear motor assembly 700, the example of linear motor assembly 800 differs in that the encoder scale tape 835 and the ring of magnet rails 855 are coupled to the gantry platform 825 and rotate relative to the base support 860 therewith around an axis of rotation (denoted by dashed line 827). An x-ray assembly (not shown) is also rigidly mounted to the gantry platform 825, and thereby is coupled to the encoder scale tape 835 and the magnet rails 855 to rotate therewith. In this example, the encoder scale tape 835 is mounted directly to a rotating outer portion of the bearing 845 in order to minimize runout stack up tolerances.

In this configuration, the coil assemblies 805 and encoder assembly 815 are mounted to the stationary base support 860. The encoder assembly 815 is positioned so that a sensor head (not shown) of the encoder assembly 815 has a field of view that includes the encoder scale tape 835 at all times during the rotation of the gantry platform 825.

The ring of magnet rails 855, each defining an arc segment of a full circle, are mounted around the circumference of the gantry platform 825, and further positioned to align during rotation of the gantry platform 825 with the stationary coil assemblies 805. Again, the distance between the two coil assemblies 805 is equal to the effective diameter of the ring of magnet rails 855. However, in some embodiments the coil assemblies 805 may be positioned asymmetrically around the stationary base support 860.

Alternatively, in some embodiments, the linear motor assembly 800 may include three or more coil assemblies mounted to the stationary base support 860. In some such embodiments, the coil assemblies may be positioned equally around the circumference of the stationary base support 860 at a distance D/2 from the axis of rotation. In other such embodiments, the coil assemblies may be positioned asymmetrically around the stationary base support 860.

The gantry platform 825 and the bearing 845 are driven to rotate relative to the base support 860 by generating a circumferentially-directed electromagnetic force between the stationary coil assemblies 805 and the rotating magnet rails 855. During rotation of the gantry platform 825, the stationary encoder scale tape 835 rotates past the encoder assembly 815, and generates signals which are received by a processor 870. The processor 870 uses these signals to determine (e.g., in real-time) the rotation angle and position of the gantry platform 825 relative to the base support 860, as well as provide an automated "homing" instruction to rotate the gantry platform 825 to a predetermined angular position.

In this configuration, electrical power and control signals may be provided to/from the coil assemblies 805 and the encoder assembly 815 via cabling 880, without the requirement of a slip ring. Additional control electronics (e.g., a motor amplifier, not shown) and the processor 870 may be mounted externally to the linear motor assembly 800.

The terms "light" and "optical" are intended to have broad meanings that can include both visible regions of the electromagnetic spectrum as well as other regions, such as, but not limited to, infrared and ultraviolet light and optical imaging, for example, of such light.

The terms "computer", "server", "processor", and "memory" all refer to electronic or other technological devices. These terms exclude people or groups of people. As used in this specification, the terms "computer readable medium," "computer readable media," and "machine readable medium," etc. are entirely restricted to tangible, physical objects that store information in a form that is readable by a computer. These terms exclude any wireless signals, wired download signals, and any other ephemeral signals.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but not limited to) a hard disk drive and/or a removable storage drive, representing a floppy diskette drive, a magnetic tape drive, an optical disk drive, a read-only compact disk (CD-ROM), digital versatile discs (DVDs), flash memory (e.g., SD cards, mini-SD cards, micro-SD cards, etc.), read-only and recordable Blu-Ray® discs, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In some embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

Some embodiments include electronic components, such as microprocessors, storage and memory that store computer program instructions in a machine-readable or computer-readable medium (alternatively referred to as computer-readable storage media, machine-readable media, or machine-readable storage media). The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The computer may also include an input device may include any mechanism or combination of mechanisms that may permit information to be input into the computer system from, e.g., a user. The input device may include logic configured to receive information for the computer system from, e.g., a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or another camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions, including application-specific integrated circuits (ASICs) and field-programmable gate arrays (FPGAs). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

The term "network" is intended to include any communication network, including a local area network ("LAN"), a wide area network ("WAN"), an Intranet, or a network of networks, such as the Internet.

The term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. More-over, features described in connection with one embodiment may be used in conjunction with other embodiments, even if not explicitly stated above.

I claim:

1. An x-ray system for at least one of breast examinations and procedures, comprising:
   a base component;
   a table configured to support a patient in a prone position and disposed proximate said base component with a space reserved therebetween;
   a rotatable x-ray assembly disposed between said base component and said table;
   a linear motor assembly operatively connected to said rotatable x-ray assembly and said base component so as to effect rotation of said rotatable x-ray assembly relative to said base component during operation;
   an encoder assembly arranged proximate to said linear motor assembly, said encoder assembly being constructed to provide information regarding at least one of an amount of rotation and a rotational position of said rotatable x-ray assembly relative to said base component; and
   a data processor communicatively coupled to said encoder assembly and to said rotatable x-ray assembly,
   wherein said rotatable x-ray assembly rotates at least partially around an active spatial region,
   wherein said table defines an opening that is positioned for a breast to extend downwards therethrough at least partially into said active spatial region,
   wherein said data processor is further configured to:
      receive x-ray data acquired from said rotatable x-ray assembly;
      receive information from said encoder assembly;
      determine at least one of an amount of rotation and a rotation position of the rotatable x-ray assembly during acquisition of the x-ray data; and
      generate a plurality of x-ray images based on the received x-ray data and at least one of the determined amount of rotation and the rotation position of the rotatable x-ray assembly.

2. The x-ray system according to claim 1, wherein said base component and said table are configured to be fixed relative to each other.

3. The x-ray system according to claim 1, wherein the linear motor assembly comprises a plurality of coil assemblies and a plurality of magnet rails positioned proximal to the plurality of coil assemblies,
   wherein said plurality of coil assemblies are rotors for the linear motor assembly, and
   wherein said plurality of magnet rails are stators for the linear motor assembly.

4. The x-ray system according to claim 3, wherein the plurality of coil assemblies are coupled to the rotatable x-ray assembly so as to rotate therewith, and the plurality of magnet rails are coupled to the base component so as to remain stationary during rotation of the x-ray assembly.

5. The x-ray system according to claim 3, wherein the plurality of magnet rails are coupled to the rotatable x-ray assembly so as to rotate therewith, and the plurality of coil assemblies are coupled to the base component so as to remain stationary during rotation of the x-ray assembly.

6. The x-ray system according to claim 1,
   wherein the encoder assembly comprises a sensor head, and the x-ray system further comprises a scale tape.

7. The x-ray system according to claim 6, wherein the sensor head is coupled to the rotatable x-ray assembly, causing the sensor head to be rotated therewith relative to the base component, and
   wherein the scale tape is coupled to the base component, causing the scale tape to be stationary during rotation of the sensor head.

8. The x-ray system according to claim 6, wherein the scale tape is coupled to the rotatable x-ray assembly, causing the scale tape to be rotated therewith relative to the base component, and
   wherein the sensor head is coupled to the base component, causing the sensor head to be stationary during rotation of the scale tape.

9. The x-ray system according to claim 1, wherein the rotatable x-ray assembly comprises:
   an x-ray source positioned to irradiate with an x-ray beam at least a portion of the active spatial region;
   an x-ray detector positioned to receive at least a portion of the x-ray beam after passing through the active spatial region; and
   a gantry that is rotated by the linear motor assembly, the x-ray source and the x-ray detector being mounted to the gantry so as to be rotated therewith.

10. The x-ray system according to claim 9, wherein the x-ray detector is a flat panel detector, the x-ray beam is a cone beam, and the x-ray system is configured to perform cone-beam computed tomography.

11. The x-ray system according to claim 9, wherein the x-ray system further comprises a shield enclosure that substantially encloses the x-ray source, the x-ray detector, and the active spatial region, and
   wherein the shield enclosure attenuates x-rays from the x-ray source sufficiently for persons to be in proximity to the shield enclosure during operation of the x-ray system without further shielding while complying with radiation safety standards.

12. A method of manufacturing an x-ray system for at least one of breast examinations and procedures, comprising:
   providing a base component;
   disposing a table proximate said base component with a space reserved therebetween, said table configured to support a patient in a prone position;
   disposing a rotatable x-ray assembly between said base component and said table; and
   connecting a linear motor assembly to said rotatable x-ray assembly and said base component so as to be operative to effect rotation of said rotatable x-ray assembly relative to said base component;
   disposing an encoder assembly proximate said linear motor assembly, said encoder assembly being constructed to provide information regarding at least one of an amount of rotation and a rotational position of said rotatable x-ray assembly relative to said base component; and
   communicatively coupling a data processor to said encoder assembly and said rotatable x-ray assembly,
   wherein said rotatable x-ray assembly rotates at least partially around an active spatial region,
   wherein said table defines an opening therethrough at a position and of a size to allow a subject to lie prone with a breast hanging pendant therethrough at least partially into said active spatial region, and
   wherein said data processor is further configured to:
      receive x-ray data acquired from said rotatable x-ray assembly;

receive information from said encoder assembly;

determine at least one of an amount of rotation and a rotation position of the rotatable x-ray assembly during acquisition of the x-ray data; and generate a plurality of x-ray images based on the received x-ray data and at least one of the determined amount of rotation and the rotation position of the rotatable x-ray assembly.

13. The method of manufacturing an x-ray system according to claim 12, wherein said base component and said table are configured to be fixed relative to each other.

14. The method of manufacturing an x-ray system according to claim 12, wherein the linear motor assembly comprises a plurality of coil assemblies and a plurality of magnet rails positioned proximal to the plurality of coil assemblies, wherein said plurality of coil assemblies are rotors for the linear motor assembly, wherein said plurality of magnet rails are stators for the linear motor assembly.

15. The method of manufacturing an x-ray system according to claim 14, wherein the plurality of coil assemblies are coupled to the rotatable x-ray assembly so as to rotate therewith, and the plurality of magnet rails are coupled to the base component so as to remain stationary during rotation of the x-ray assembly.

16. The method of manufacturing an x-ray system according to claim 14, wherein the plurality of magnet rails are coupled to the rotatable x-ray assembly so as to rotate therewith, and the plurality of coil assemblies are coupled to the base component so as to remain stationary during rotation of the x-ray assembly.

17. A method of performing a breast procedure, comprising:

receiving x-ray data acquired from a rotatable x-ray assembly, said rotatable x-ray assembly disposed between a base component and a table configured to support a patient in a prone position;

receiving information from an encoder assembly, said encoder assembly being arranged proximate to a linear motor assembly that is operatively connected to said rotatable x-ray assembly and said base component so as to effect rotation of said rotatable x-ray assembly relative to said base component during operation of the x-ray assembly;

determining at least one of an amount of rotation and a rotation position of the rotatable x-ray assembly during acquisition of the x-ray data; and generating a plurality of x-ray images based on the received x-ray data and at least one of the determined amount of rotation and the rotation position of the rotatable x-ray assembly.

18. The method of performing a breast procedure according to claim 17, further comprising rotating the rotatable x-ray assembly to a particular position corresponding to a previously-generated particular x-ray image, based on information from the encoder assembly received during acquisition of the particular x-ray image and further based on a current rotation position determined from information received from the encoder assembly.

* * * * *